United States Patent [19]

Müller et al.

[11] Patent Number: 5,670,049
[45] Date of Patent: Sep. 23, 1997

[54] NUCLEOTIDE-CONTAINING SORBENT FOR AFFINITY CHROMATOGRAPHY

[75] Inventors: Egbert Müller, Erzhausen; Jürgen Hemberger, Aschaffenburg; Michael Morr, Wolfenbüttel, all of Germany

[73] Assignee: Merck Patent Gesellschaft Mit Beschrankter Haftung, Darmstadt, Germany

[21] Appl. No.: 619,687

[22] PCT Filed: Sep. 21, 1994

[86] PCT No.: PCT/EP94/03157

§ 371 Date: Apr. 1, 1996

§ 102(e) Date: Apr. 1, 1996

[87] PCT Pub. No.: WO95/09694

PCT Pub. Date: Apr. 13, 1995

[51] Int. Cl.[6] .................................................. B01D 15/08
[52] U.S. Cl. .................... 210/635; 210/656; 210/198.2; 210/502.1
[58] Field of Search ................... 210/635, 656, 210/198.2, 502.1; 502/401, 402, 403, 404

[56] References Cited

U.S. PATENT DOCUMENTS

| | | | |
|---|---|---|---|
| 3,663,263 | 5/1972 | Bodre | 210/198.2 |
| 3,808,125 | 4/1974 | Good | 210/198.2 |
| 4,029,583 | 6/1977 | Ho Chang | 210/198.2 |
| 4,045,353 | 8/1977 | Kosaka | 55/386 |
| 4,140,653 | 2/1979 | Imura | 210/198.2 |
| 4,202,775 | 5/1980 | Abe | 210/287 |
| 4,246,351 | 1/1981 | Miyake | 210/681 |
| 4,324,689 | 4/1982 | Shah | 210/198.2 |
| 4,330,440 | 5/1982 | Ayers | 210/198.2 |
| 4,332,694 | 6/1982 | Kalal | 435/180 |
| 4,335,226 | 6/1982 | Muller | 210/656 |
| 4,352,884 | 10/1982 | Nakashima | 210/198.2 |
| 4,406,870 | 9/1983 | Miyake | 210/681 |
| 4,415,631 | 11/1983 | Schutijser | 210/198.2 |
| 4,551,245 | 11/1985 | Ramsden | 210/198.2 |
| 4,710,525 | 12/1987 | Kraemer | 523/201 |
| 4,737,533 | 4/1988 | Charmot | 264/311.11 |
| 4,756,834 | 7/1988 | Muller | 210/635 |
| 4,767,529 | 8/1988 | Boos | 210/198.2 |
| 4,829,101 | 5/1989 | Kraemer | 523/201 |
| 4,882,048 | 11/1989 | Blaschke | 210/198.2 |
| 4,882,226 | 11/1989 | Schutyser | 210/198.2 |
| 4,908,137 | 3/1990 | Chen | 210/679 |
| 4,937,000 | 6/1990 | Bomer | 210/656 |
| 5,135,650 | 8/1992 | Hjerten | 210/198.2 |

FOREIGN PATENT DOCUMENTS

| | | | |
|---|---|---|---|
| 6199 | 9/1980 | European Pat. Off. | 210/198.2 |
| 337144 | 3/1989 | European Pat. Off. | 210/198.2 |
| 346865 | 12/1989 | European Pat. Off. | 210/198.2 |
| 356838 | 7/1990 | European Pat. Off. | 210/198.2 |
| 425848 | 5/1991 | European Pat. Off. | 210/198.2 |
| 467339 | 7/1991 | European Pat. Off. | 210/198.2 |
| 2440956 | 6/1980 | France | 210/198.2 |
| 2631849 | 12/1989 | France | 210/198.2 |
| 1814598 | 12/1968 | Germany | 210/198.2 |
| 2337312 | 2/1975 | Germany | 210/198.2 |
| 468814 | 3/1993 | Sweden | 210/198.2 |
| WO9313220 | 7/1993 | WIPO | 210/198.2 |

OTHER PUBLICATIONS

Derwent Abstract of Japan Patent 62 267 663 vol. 12 No. 147 (P-698) May 1988.
Derwent Abstract of Japan Patent 93-285445 Aug. 10, 1993.
Derwent Abstract of Japan Patent 86-086136.
Patent Abstracts of Japan, JP 57077958, May 1982.
Derwent Abstract of Japan Patent JP 5247123 (1993).

*Primary Examiner*—Ernest G. Therkorn
*Attorney, Agent, or Firm*—Millen, White, Zelano & Branigan, P.C.

[57] ABSTRACT

The invention relates to sorbents for for [sic] affinity chromatography which are based on hydroxyl-containing base supports on whose surfaces polymers are covalently bonded, characterized in that
a) the base support contains aliphatic hydroxyl groups,
b) the covalently bonded polymers are bound to the base support by a terminal monomer unit,
c) the polymers contain monomer units of the formula II
d) the monomer units are linked linearly,

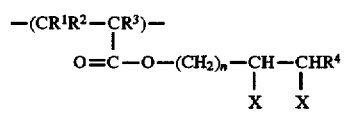

in which $R^1$, $R^2$ and $R^3$ independently of one another are H or $CH_3$,
$R^4$ is H, $C_1$–$C_5$-alkyl or $C_6$–$C_{12}$-aryl,
n is an integer between 1 and 5 and
one of the radicals X is OH and the other radical X is a nucleoside-containing radical,
and to their preparation and use, especially for affinity chromatography.

11 Claims, No Drawings

NUCLEOTIDE-CONTAINING SORBENT FOR AFFINITY CHROMATOGRAPHY

The invention relates to sorbents for affinity chromatography which comprise nucleosides or nucleotides as affinity ligands, and to phosphoric acid-containing intermediate compounds for their preparation and the use thereof.

BACKGROUND OF THE INVENTION

For biological interactions, for example the mechanisms of cell recognition, an important role is played by glycoproteins, which frequently contain sialic acid. The oligosaccharide components of these glycoproteins often possess complex structures. Consequently, the in vitro synthesis of such oligosaccharides by methods of organic chemistry is, owing to the introduction and elimination of protecting groups, for example, extremely complex. Their isolation from natural substances is normally of similar complexity. As a consequence, in vitro syntheses entail the combination of organic chemical steps with biochemical steps. The biochemical synthesis steps exploit the ability of enzymes to produce defined chemical structures in a specific manner, without the need to introduce protecting groups. For such reactions, various enzymes from the group of the glycosyltransferases are required. For example, sialic acid residues can be attached to mono- or oligosaccharides by using sialyltransferases.

The isolation of the glycosyltransferases, for example sialyl-, glucosyl-, acetylglucosamine-, galactosyl-, galactosamine, mannosyl- or fucosyl-transferase, is best carried out with the aid of affinity chromatography, preference being given to the use of immobilized nucleoside diphosphates, nucleosides, mono- or oligo-nucleotides as affinity ligands. For sialyltransferase, cytidine diphosphate (CDP) is the preferred affinity ligand.

Nucleoside-containing affinity ligands are also suitable for enriching other enzymes, for example dehydrogenases, oxidases, kinases or transaminases.

Prior art affinity chromatography sorbents contain polysaccharides, for example agarose, as base supports, to which CDP is attached via an aminohexyl radical as spacer. This spacer is necessary for the interaction of affinity ligand with enzyme. However, owing to the hydrophobic nature of the spacer, unwanted interactions occur which reduce the yield of enzyme and its activity. The object is therefore to provide improved nucleoside-containing affinity supports for the purification of enzymes, for example glycosyltransferases.

The application DE 43 10 964 discloses oxirane-containing activated support materials in which monomers of the formula I are grafted onto a hydroxyl-containing matrix

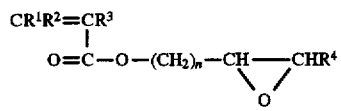    I in which

R$^1$, R$^2$ and R$^3$ independently of one another are H or CH$_3$,

R$^4$ is H, C$_1$–C$_5$-alkyl or C$_6$–C$_{12}$-aryl and n is an integer between 1 and 5.

SUMMARY OF THE INVENTION

It has been found that it is possible, from these activated support materials, to produce separation materials for affinity chromatography by the combination of individual steps which are known per se. The resulting separation materials have improved properties.

The invention relates to separation materials for affinity chromatography which are based on hydroxyl-containing base supports on whose surfaces polymers are covalently bonded, characterized in that a) the base support contains aliphatichydroxyl groups, b) the covalently bonded polymers are bound to the base support by a terminal monomer unit, c) the linear polymers contain monomer units of the formula II

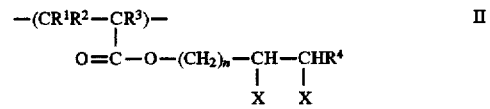    II in which

R$^1$, R$^2$ and R$^3$ independently of one another are H or CH$_3$,

R$^4$ is H, C$_1$–C$_5$-alkyl or C$_6$–C$_{12}$-aryl, n is an integer between 1 and 5 and one of the radicals X is OH and the other radical X is a nucleoside-containing radical, for example a nucleoside diphosphate radical, a mono- or oligonucleotide radical or a nucleoside radical.

In particularly preferred embodiments, the nucleoside-containing radical X is derived from one of the following compounds: CDP, UDP, GDP, AMP, ADP, ATP, cyclo-AMP.

The invention relates to the use of these separation materials according to the invention for affinity chromatography.

The invention relates to processes for the preparation of a nucleoside-containing sorbent, characterized by the following process steps:

a) graft polymerization of monomers of the formula I onto a hydroxyl-containing base support, with the participation of cerium(IV),

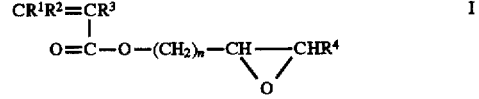    I in which

R$^1$, R$^2$ and R$^3$ independently of one another are H or CH$_3$,

R$^4$ is H, C$_1$–C$_5$-alkyl or C$_6$–C$_{12}$-aryl and n is an integer between 1 and 5;

b) reaction of the epoxide group-containing support from process step a) with phosphoric acid or with an alkali metal salt of phosphoric acid or with ammonia; and c) introduction of nucleoside-containing radicals into the product obtained in step b).

In one preferred embodiment, the reaction of step b) takes place with phosphoric acid; the phosphorylated support is subsequently converted into an alkylated ammonium salt by addition of an excess of a tertiary alkylamine or of pyridine. This ammonium salt is reacted under dehydrating conditions with a nucleotide or oligonucleotide.

In a further embodiment, the reaction of step b) takes place with ammonia. The nucleotide radical is then introduced in the form, for example of 6-chloropurine riboside. The resulting purine derivative can be reacted by methods which are known per se, for example, to give a support-bound AMP, ATP or cyclic AMP derivative. Analogous reactions to give other nucleoside-containing compounds are also known.

The invention additionally relates to phosphoric acid ester derivatives of a graft polymer on the basis of hydroxyl-containing base supports on whose surfaces polymers are covalently bonded, characterized in that
a) the base support contains aliphatichydroxyl groups,
b) the covalently bonded polymers are attached to the base support by a terminal monomer unit,
c) the linear polymers contain monomer units of the formula III

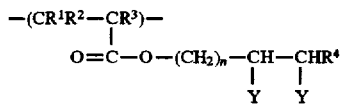

$$-(CR^1R^2-CR^3)-$$
$$\quad\quad\quad |$$
$$O=C-O-(CH_2)_n-CH-CHR^4$$
$$\quad\quad\quad\quad\quad\quad\quad |\quad\quad |$$
$$\quad\quad\quad\quad\quad\quad\quad Y\quad\quad Y$$

in which
$R^1$, $R^2$ and $R^3$ independently of one another are H or $CH_3$.
$R^4$ is H, $C_1$–$C_5$-alkyl or $C_6$–$C_{12}$-aryl,
n is an integer between 1 and 5 and
one of the radicals Y is OH and the other radical Y is $PO_4H_2$.

The invention relates, finally, to the use of a novel phosphoric acid ester derivative of a grafted polymer for the preparation of an affinity chromatography sorbent according to the invention, and as a cation exchanger for liquid chromatography.

The first process step either involves the reaction of phosphoric acid or the salts thereof with epoxide groups of the activated support materials described in DE 43 10 964 to give phosphoric acid monoester derivatives of these support materials, or the epoxide groups are reacted with ammonia to give the hydroxyamine derivative. Through the content of oxirane radicals in the activated support materials and the choice of the reaction conditions (quantity of phosphoric acid/phosphate; reaction period and temperature) it is possible to adjust the degree of substitution of the phosphoric acid monoester derivative of the support material. The degree of substitution in the reaction with ammonia can be varied in a similar manner. Any excess oxirane groups are removed by customary methods, for example by reaction with mercaptoglycerine or by treatment with dilute sulfuric acid.

The phosphoric acid monoester derivatives of the support material which are prepared by this process can also be used as cation exchangers.

In biochemistry, the term nucleoside is used to refer to N-glycosides of the pyrimidine bases thymine, uracil and cytosine and of the purine bases guanine and adenine with ribose or 2-deoxyribose. Nucleotides are the phosphoric esters of these nucleosides. Nucleoside diphosphates contain a further phosphoric acid radical which is attached via a pyrophosphate linkage to the first phosphoric acid radical. Oligonucleotides contain a plurality of nucleotides, which can be identical or different, and which are linked by phosphoric acid diester linkages. In accordance with the invention, the terms nucleoside, nucleotide and oligonucleotide also refer to compounds wherein, instead of the bases mentioned, other purine or pyrimidine bases are present, for example hypoxanthine, 5-methylcytosine or N-2-methylguanosine, or wherein the ribose or 2-deoxyribose is replaced by another sugar radical or a sugar alcohol such as ribitol. Analogous compounds of this kind are known to the person skilled in the art. In their entirety, these compounds are encompassed according to the invention by the term nucleoside-containing compounds or radicals. Examples of such nucleoside-containing compounds are adenosine, AMP, ADP, ATP, cyclo-AMP, CDP, UDP, GDP, NAD(H), NADP (H), FMN or FAD.

Ester linkages are produced from an acid and an alcohol by elimination of water; correspondingly, pyrophosphate linkages are produced from two phosphoric acid compounds. The most common dehydrating agents include, for example, the carbodiimides, such as dicyclohexylcarbodiimide. 1,1'-Carbonyldiimidazole is preferably used for this purpose. Other methods of dehydration employ activated intermediates, such as acid halides or anhydrides. The specifics of such methods and suitable variants thereof are known to the person skilled in the art, for example from current handbooks. To form pyrophosphate linkages between the phosphoric acid ester derivative containing monomer units of formula III and the nucleotides, preference is given to the method of Michelson (1964), Biochim. Biophys. Acta 91, 1 ff. In this method, the phosphoric esters are converted using tertiary amines or using quaternary ammonium hydroxide into the corresponding primary salts. In this context, preference is given to the use of tri-n-butylamine or of methyltri-n-octylammoniumhydroxide.

Further syntheses for the preparation of nucleoside derivatives are known to the person skilled in the art; these can be applied in a suitable manner to the reaction with the activated support materials known from DE 43 10 964, in which case the phosphoric acid derivatives or amino derivatives of these supports are used as preferred intermediates. Such reactions include the alkylation of the amino derivative with 6-chloropurine riboside, 2',3'-isopropylidene-6-chloropurine riboside or 6-chloro-AMP. In the latter case, the support-bound AMP derivative is obtained directly. The protected riboside compound can then be phosphorylated in accordance with Yoshikawa, M. Yoshikawa et al., Tetrahedron Lett. (1967) 1967, 5065; M. Yoshikawa and T. Karo (1967) Bull. Chem. Soc. Jpn. 40, 2849; K. Kusashio and M. Yoshikawa (1968) Bull. Chem. Soc. Jpn. 41, 142; M. Yoshikawa et al. (1969) Bull. Chem. Soc. Jpn. 42, 3505. The protecting group of the 2',3'-isopropylidene derivative can be eliminated after the 5'-tosylation. In all cases, the subsequent derivatization reactions can be carried out by customary methods of nucleoside chemistry. These include the ATP synthesis of J. Ludwig ((1981) Acta Biochim. Biophys. Acad. Sci. Hung. 16, 131–133) or the formation of pyrophosphates or triphosphate from the AMP derivative by means of dehydrating agents such as, for example, dicyclohexylcarbodiimide or carbonyldiimidazole. It is also possible to prepare cyclic phosphate derivatives such as cyclo-AMP derivatives. One example of a further literature reference which may be mentioned is H. Guilford et al. (1972) Chemica Scripta 2, 165–170.

Even without further statements it is assumed that a person skilled in the art will be able to utilize the above description in its widest context. Consequently, preferred embodiments are to be interpreted merely as descriptive and in no way as a disclosure which is in any sense limiting.

The complete disclosure of all applications, patents and publications listed above and below, and of the corresponding application DE 43 33 674 submitted on 2 Oct. 1993, are incorporated into this application by reference.

The examples which follow are intended to illustrate the subject matter in more detail; these examples do not constitute any restriction of the subject matter of the invention.

EXAMPLES

Example 1

Preparation of an Oxirane-activated Support Starting From Fractogel®-TSKHW 65 (S)

To a suspension of 50 ml of sedimented Fractogel®-TSK HW 65 (S) and 25 ml of water are mixed, vigorous stirring at room temperature, with 2 g of ammoniumcerium(IV)

nitrate (dissolved in 25 ml of 2M $HNO_3$). After 1 minute, a solution of 3 g of 2,3-epoxypropyl methacrylate in 30 ml of dioxane is added. Stirring is continued for 3 hours. The reaction suspension is then washed, first with distilled water and subsequently with 0.05M EDTA solution.

Example 2

Synthesis of a Support Material Containing Phosphate Groups 5 g of dried gel prepared according to Example 1 are suspended in 20 ml of water, and 8 ml of phosphoric acid (85%) are added. The suspension is shaken at room temperature for 3 to 4 hours. The reaction product is filtered off with a glass frit (G3) and washed to neutrality with water.

The reaction product is subsequently treated, while shaking, with 1 ml of mercaptoglycerine in 0.1M sodium phosphate buffer pH 7.5 (3 days, room temperature), in order to remove unreacted oxirane groups.

The phosphate group-containing support material is subsequently washed thoroughly with water. It contains 30 μmol of phosphate/g of support material.

Example 3

Synthesis of a Phosphate Group-containing Support Material with High Phosphate Content 5 g of dried gel prepared according to Example 1 are reacted as described in Example 2, but the reaction with the phosphoric acid is carried out for 15 hours. The phosphate group-containing support material which results contains 40 μmol of phosphate/g of support material.

Example 4

Synthesis of a Support Material Derivatized with Cytidine 5'-diphosphate (CDP)

Step 1: Tri-n-butylammonium salt of the derivatized support material

The moist reaction product from Example 2 is suspended in 30 ml of water, 0.5 ml of tri-n-butylamine is added, and the mixture is shaken at room temperature for 1 hour. The product is then filtered on a glass frit (G2) and washed three times with 50 ml of acetone. The solid residue is dried overnight under vacuum (5–7 torr) at 50° C. in a 250 ml round-bottomed flask.

Step 2: Methyl-tri-octylammonium salt of CMP 4.2 g of methyltrioctylammonium chloride are dissolved in 100 ml of methanol and converted by way of a column (DOWEX® 1X2, 200–400 mesh; OH form) into the quaternary base. This solution is added to a suspension of 3.23 g of CMP in 250 ml of methanol. The resulting methyltrioctylammonium salt of CMP is concentrated.

Step 3: Diphenylpyrophosphate-activated CMP 1 mmol of the methyltrioctylammonium salt of CMP from step 2 is dissolved in a mixture of 7 ml of dioxane and 3 ml of N,N-dimethylformamide. With exclusion of moisture, 0.3 ml of diphenylphosphoryl chloride and 0.45 ml of tri-n-butylamine are added to the solution, and the mixture is shaken for 3 hours. The solvent is then removed under vacuum in a rotary evaporator and the residue is treated with 30 ml of diethyl ether. The suspension is cooled at 0° C. for 1 hour and the ether phase is decanted and discarded. The residue is dried in vacuo, redissolved in 2 ml of dioxane and again dried in vacuo.

Step 4: Pyrophosphate derivative of CMP and of derivatized support material

The derivatized support material from step 1 is suspended in 30 ml of pyridine, a solution of 0.5 mmol of the diphenylpyrophosphate-activated CMP from step 3 in 10 ml of pyridine is added to the suspension with exclusion of moisture, and the mixture is shaken at room temperature overnight. The reaction product is filtered off with a glass frit (G2) and washed with 250 ml of methanol, 100 ml of saturated aqueous sodium hydrogen carbonate solution and 1000 ml of water.

The resulting material contains 25 μmol of cytidine/g moist weight (measured by UV absorption at 267 nm after hydrolysis (1N HCl; 2 hours at 110° C.) and subsequent neutralization with 1N NaOH).

Example 5

Synthesis of a Support Material Derivatized with Guanosine 5'-diphosphate (GDP)

Step 1: Tri-n-butylammonium salt of the derivatized support material

The procedure of this step is identical with that of step 1 of Example 4.

Step 2: Tri-n-butylammonium salt of GMP 3 g of GMP (free acid) and 1.1 g of tri-n-butylamine are heated in 250 ml of methanol until the solution is clear; the solution is then concentrated to dryness.

Step 3: Diphenylpyrophosphate-activated GMP 1 mmol of the tri-n-butylammonium salt of GMP from step 2 is dissolved in a mixture of 7 ml of dioxane and 3 ml of N,N-dimethylformamide. 0.3 ml of diphenylphosphoryl chloride and 0.45 ml of tri-n-butylamine are added to the solution, with exclusion of moisture, and the mixture is shaken for 3 hours. The solvent is then removed under vacuum in a rotary evaporator and the residue is treated with 30 ml of diethyl ether. The suspension is cooled at 0° C. for 1 hour and the ether phase is decanted and discarded. The residue is dried in vacuo, redissolved in 2 ml of dioxane and dried in vacuo again.

Step 4: Pyrophosphate derivative of GMP and of derivatized support material

The derivatized support material of step 1 is suspended in 30 ml of pyridine, a solution of 0.5 mmol of the diphenylpyrophosphate-activated GMP from step 3 in 10 ml of pyridine is added to the suspension, with exclusion of moisture, and the mixture is shaken at room temperature overnight. The reaction product is filtered off with a glass frit (G2) and washed with 250 ml of methanol, 100 ml of saturated aqueous sodium hydrogen carbonate solution and 1000 ml of water.

The resulting material contains 30 μmol of guanosine/g moist weight (measured by UV absorption at 270 nm after hydrolysis (1N HCl; 2 hours at 110° C.) and subsequent neutralization with 1N NaOH).

Example 6

Synthesis of an Amino-containing Support Material 35 g of dried gel prepared according to Example 1 are shaken at room temperature for 5 days in 200 ml of concentrated aqueous ammonia solution. During this procedure, the progress of the reaction can be checked as follows: a dry sample of the reaction mixture is boiled with pyridine. While epoxide groups are still present, the support undergoes a brown to yellow discoloration. Following complete reaction, the support remains colorless.

The reaction product is subsequently filtered off with suction on a G3 frit and washed with methanol and acetone. It is then dried in vacuo (10–15 mbar) at 60°–70° C.

The reaction product has a nitrogen content of 1.3%. On heating with an ethanolic ninhydrin solution, the support changes color to violet.

Example 7

Synthesis of a Purine Riboside-containing Support Material 36 g of the amino derivative prepared according to Example 6 are suspended in 150 ml of absolute ethanol, and the suspension is heated at reflux for 15 hours with 3.6 g of 6-chloropurine riboside and 3.6 ml of triethylamine.

The reaction product is subsequently filtered off on a G3 frit and washed with methanol and acetone. The reaction product is transferred to a round-bottomed flask and dried in vacuo (10–15 mbar) at 60°–70° C.

The degree of coupling is about 97%.

Example 8

Synthesis of an AMP-containing Support Material (Phosphorylation According to Yoshikawa)

125 ml of anhydrous triethyl phosphate are added to the product from Example 7, and 1.8 ml of freshly distilled phosphorus oxychloride are added with stirring at 0° C. The mixture is stirred at 0° C. for 3 hours and then at 4° C. for one hour. Excess phosphorus oxychloride is subsequently distilled off in vacuo (10–15 mbar).

To prepare the AMP derivative, the reaction suspension is then poured slowly, with stirring at 10° C., into 500 ml of aqueous sodium hydrogen carbonate solution (50 g/l). In this procedure, the pH falls from 7.8 to 7.2. After 30 minutes, the product is filtered off with suction over a G3 frit and washed with water. Treatment of the sodium salt on the frit with 0.1N aqueous HCl gives the free acid (AMP derivative of the support) which is washed on the frit with water, methanol and acetone and dried at 70° C. in vacuo (10–15 mbar).

Example 9

Synthesis of a Cyclo-AMP-containing Support Material

The dried product from Example 8 is suspended in 150 ml of anhydrous pyridine in an apparatus including stirrer and reflux condenser, and 5.4 g of dicyclohexylcarbodiimide are added. The mixture is heated at reflux for 4 hours. The product is then filtered off with suction on a G3 frit and washed with dichloromethane, methanol, hot methanol (to dissolve out the dicyclohexylurea), water, saturated aqueous sodium hydrogen carbonate solution, 1M aqueous potassium dihydrogen phosphate solution (pH 4) and water. The moist gel is stored in 20% (v/v) aqueous ethanol with the addition of 0.1M NaCl.

Example 10

Synthesis of an ATP-containing Support Material (ATP Synthesis According to J. Ludwig (1981) Acta Biochim. Biophys. Acad. Sci. Hung. 6, 131–133)

The product from Example 8 (chlorine derivative, i.e. prior to hydrolysis) is reacted with the tri-n-butylammonium salt of pyrophosphoric acid.

A mixture of 0.5M bis-tri-n-butylammonium salt of pyrophosphoric acid in anhydrous DMF and tri-n-butylamine is added with shaking. After a vigorous shaking for 5 minutes, the suspension is hydrolyzed with 1M triethylammonium hydrogen carbonate buffer (pH 7.5) and, after 0.5 hour, the product is filtered off with suction over a G3 frit and washed with water, saturated sodium hydrogen carbonate solution and water.

The yield of ATP is ~60 % (P analysis).

Use Example A: Separation of Sialyltransferase From Bovine Colustrum

A Superformance® column (I.D. 1.6 cm) is packed with 10 g of CDP-containing support material according to Example 4 and equilibrated with 10 mM MES buffer pH 6.8 containing 25% glycerol. Bovine colustrum from the 1st day following birth is defatted by centrifugation and dialyzed exhaustively against the same buffer. About 1 l of dialyzed colustrum is applied to the column with a flow rate of 1 ml/min. Elution is carried out with a step gradient of 1.0M NaCl.

The activity of the sialyltransferase is determined via the transfer of CMP-[$^{14}$C]-sialic acid to lactose. For this determination, 50 µl of enzyme sample are incubated at 37° C. for 15 minutes with 30 µl of MES buffer (final concentration: 50 mM MES, 10 mM $MnCl_2$, pH 6.8), 10 µl of 0.8M lactose and 10 µl of CMP-[$^{14}$C]-sialic acid (0.05 µCi). The reaction batch is stopped with 1 ml of ice-cold 5 mM potassium phosphate buffer pH 7.0 and is chromatographed on a 1 ml column with Dowex 1X8-200. Under these conditions, CMP-[$^{14}$C]-sialic acid is retarded on the column while the product [$^{14}$C]-sialyl lactose can be isolated in the nonbinding fraction.

1 unit of sialyltransferase activity is defined as the transfer of 1 µmol of [$^{14}$C]-sialic acid per minute. 0.2 U of sialyltransferase are bound per g of support material. This binding capacity is 50% greater than that of a comparison material (CDP coupled to BrCN-Sepharose). The bound activity was eluted using 1.0M NaCl with a yield of 75%, while the comparison material only showed a recovery rate of not more than 8% (elution with 2.0M NaCl).

Use Example B: Separation of 1¾-fucosyltransferase From Human Milk 1000 ml of human milk are defatted by centrifugation and dialyzed exhaustively at 4° C. against 10 mM Na cacodylate, 10 mM $MgCl_2$, 20% glycerol pH 6.8. The prepurification of the transferase is carried out by a method which has been described (Eppenberger-Castori et al., Glycoconjugate J., 6, pp. 101–114, 1990) by chromatography on Fractogel® $SO_3$ (from E. Merck).

The determination of the fucosyltransferase activity is carried out by analogy with Example 6 using GDP-[$^{14}$C]-fucose as substrate.

Active fractions from the $SO_3$ chromatography are desalinated by dialysis and purified by affinity chromatography on GDP support material according to Example 5. For this purpose, a Superformance® column (I.D. 1.0 cm) is packed with 2 ml of support material and equilibrated with 10 mM Na cacodylate, 10 mM $MgCl_2$, 20% glycerol pH 6.8 (0.5 ml/min). Following application of the sample, the column is washed exhaustively with equilibration buffer and eluted with a NaCl gradient (0–1.5M NaCl, 20 column volumes, 0.2 ml/min).

The yield is about 83% for an approximately 450-fold enrichment. The fucosyltransferase can be seen as the dominant band in SDS gel electrophoresis (MW 47 kD).

We claim:

1. A separation material for affinity chromatography comprising a hydroxyl-containing base support on the surface of which polymers are covalently bonded, wherein
    a) the base support contains aliphatic hydroxyl groups,
    b) the covalently bonded polymers are bound to the base support by a terminal monomer unit, c) the linear polymers contain monomer units of the formula II

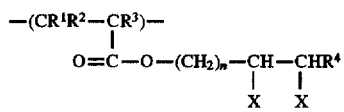

in which $R^1$, $R^2$ and $R^3$ independently of one another are H or $CH_3$, $R^4$ is H, $C_1$–$C_5$-alkyl or $C_6$–$C_{12}$-aryl, n is an integer between 1 and 5 and one of the radicals X is OH and the other radical X is a nucleoside-containing radical.

2. The separation material according to claim 1, wherein the nucleoside-containing radical X is a radical of formula IV:

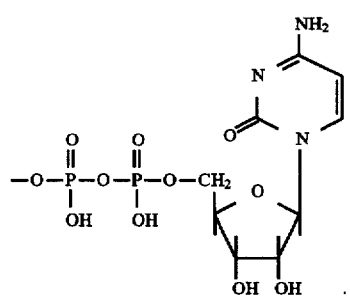

3. The separation material according to claim 1, wherein the nucleoside-containing radical X is a radical of formula V:

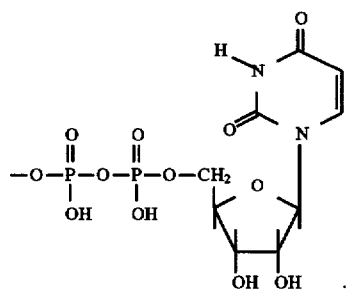

4. The separation material according to claim 1, wherein the nucleoside-containing radical X is a radical of formula VI:

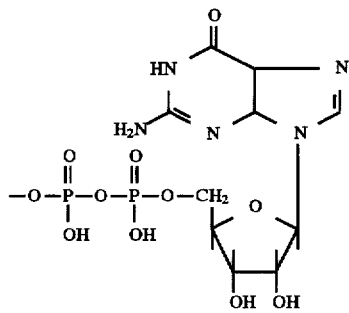

5. The separation material according to claim 1, wherein the nucleoside-containing radical X is a radical of formula VII in which m is 1, 2 or 3:

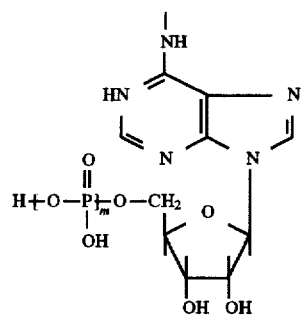

6. The separation material according to claim 1, wherein the nucleoside-containing radical X is a radical of formula VIII:

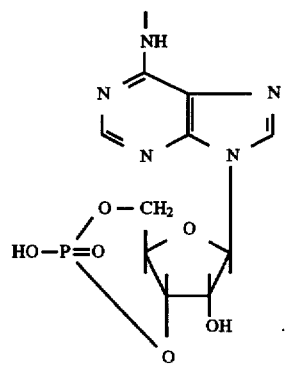

7. The separation material of claim 1, wherein the nucleoside-containing radical X is adenosine, AMP, ADP, ATP, cyclo-AMP, CDP, UDP, GDP, NAD(H), NADP(H), FMN or FAD.

8. A process for the preparation of a separation material of claim 1 comprising:

a) graft polymerizing monomers of the formula I onto a hydroxyl-containing base support, in the presence of cerium(VI) ions,

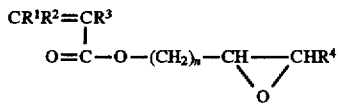

in which

R¹, R² and R³ independently of one another are H or $CH_3$,

R⁴ is H, $C_1$–$C_5$-alkyl or $C_6$–$C_{12}$-aryl, n is an integer between 1 and 5;

b) reacting the epoxide group-containing product of a) with phosphoric acid or with an alkali metal salt of phosphoric acid or with ammonia; and c) introducing nucleoside-containing radicals into the product of b).

9. The process of claim 8, wherein the reacting, (b), is with phosphoric acid, the phosphorylated product is converted to an alkylated ammonium salt by addition of an excess of tertiary alkylamine or pyridine and the ammonium salt is reacted under dehydrating conditions with a nucleotide or oligonucleotide to introduce the nucleoside-containing radical.

10. The process of claim 8, wherein the reacting, (b), is with ammonia.

11. A process for separation of materials by affinity chromatography which comprises contacting the materials to be separated with a separation material according to claim 1.

* * * * *